(12) United States Patent
Brust et al.

(10) Patent No.: US 6,210,958 B1
(45) Date of Patent: Apr. 3, 2001

(54) TEMPERATURE REGULATING BLOCK WITH RECEIVERS

(75) Inventors: Ruediger Brust, Ziethen; Juergen Lenz, Hamburg, both of (DE)

(73) Assignee: Eppendorf-Netheler-Hinz, GbmH, Hamburg (DE)

( * ) Notice: Subject to any disclaimer, the term of this patent is extended or adjusted under 35 U.S.C. 154(b) by 0 days.

(21) Appl. No.: 09/297,874
(22) PCT Filed: Nov. 7, 1997
(86) PCT No.: PCT/EP97/06196
§ 371 Date: May 10, 1999
§ 102(e) Date: May 10, 1999
(87) PCT Pub. No.: WO98/20976
PCT Pub. Date: May 22, 1998

(30) Foreign Application Priority Data

Nov. 8, 1996 (DE) .............................. 196 46 116

(51) Int. Cl.[7] .................................... C12M 1/34
(52) U.S. Cl. ..................... 435/287.2; 435/288.3; 435/303.1; 422/50; 422/109; 165/201; 165/253; 165/267; 935/85
(58) Field of Search ............... 435/283.1, 286.2, 435/287.2, 288.3, 303.1; 422/50, 109; 165/201, 253, 267; 935/85

(56) References Cited

U.S. PATENT DOCUMENTS

| | | | |
|---|---|---|---|
| 3,556,731 | 1/1971 | Martin | 23/253 |
| 5,061,630 | 10/1991 | Knopf et al. | 435/290 |
| 5,399,840 | 3/1995 | Goeddeke | 219/521 |
| 5,430,957 | 7/1995 | Eigen | 34/423 |
| 5,525,300 | 6/1996 | Danssaert et al. | 422/99 |
| 6,054,263 | * 4/2000 | Danssaert et al. | 435/4 |

FOREIGN PATENT DOCUMENTS

WO 92/0497   4/1992   (WO).

* cited by examiner

Primary Examiner—David A. Redding
(74) Attorney, Agent, or Firm—Brown & Wood, LLP (57) ABSTRACT

A temperature regulating block for lab thermostatting systems has a receiving side with two kinds of seats in the form of differently shaped recesses to implement large-area contact-making seating of filled lower zones of two differently shaped kinds of receptacles filled with sample liquid. At least one temperature regulator is in contact with the block. The two kinds of seats are arranged in a regular, two-dimensional grid such that a seat of one kind in each case is located between four seats of the other kind.

6 Claims, 5 Drawing Sheets

TEMPERATURE REGULATING BLOCK WITH RECEIVERS

FIELD OF THE INVENTION

The present invention relates to a temperature regulating block for lab thermostatting systems having a receiving side with recessed seats to implement large-area contact seating of filled, lower zones of receptacles filled with sample liquids and having at least one temperature regulator with which it is in contact.

BACKGROUND OF THE INVENTION

A temperature regulating block of this general type is known from U.S. Pat. No. 5,525,300 wherein the seats are identical recesses receiving one kind of receptacles and are in rows and columns in the temperature regulating block.

This has the drawback, first, that only one kind of receptacle can be used. If, as occurs in the lab, different kinds of receptacles must be used, the temperature regulating block must then be replaced because inadequate thermal contact would result if the containers were less than optimally matched to the recesses. Moreover, the recesses forming the seats are significantly separated from one another in this known design. Accordingly, the temperature regulating block is quite heavy and its heat capacity is high. The temperature of such a temperature regulating block can only be changed slowly. Another drawback is the excellent thermal conductivity of the block, entailing high heat flux when temperature gradients are produced and demanding large energies for heating and cooling. If the temperature regulating block is used at a regulated temperature differential by multiple temperature regulators to produce a temperature gradient, then the heat flux between the temperature regulators also will exist between the recesses, and the temperature distribution may be non-uniform.

SUMMARY OF THE INVENTION

An object of the present invention is to provide a temperature regulating block of the type mentioned above which assures rapidly a state of optimal temperature distribution for different vessels.

The invention provides two kinds of recesses to seat different receptacles. Accordingly, the temperature regulating block accepts receptacles of one kind as well as of the other, optionally even simultaneously. As a result, the thermostatting systems for lab work can be operated in a significantly more flexible manner. Because of the large number of mutually nesting recesses, the temperature regulating block is made substantially thinner, and its overall weight is relatively very modest. Thereby its heat capacity is reduced and the temperature regulating block can be made to more rapidly assume the desired temperatures. Illustratively, samples received in a temperature regulating block can be rapidly and consecutively made to assume different temperature levels. By thinning the material of the temperature regulating block, its thermal conductivity is reduced, i.e., its thermal impedance is raised. If the temperature regulating block is operated with several temperature regulators in turn operated in different manners to implement a temperature gradient, then a slight heat flux suffices because of the high thermal impedance, and consequently the energy consumption for heating and cooling can be substantially reduced. By situating the recesses at the receptacle receiving side, the thick segments of the temperature regulating block are reduced, especially at the seating side. When differentially heating the temperature regulating block for achieving a temperature gradient, there is a lesser heat flux in that zone than in the lower segment of the temperature regulating block. As a result, uniformity of temperature distribution is improved.

By arranging the seats of one shape in a predetermined grid configuration in the temperature regulating block, the block is usable with such receptacles mounted in a predetermined grid and illustratively connected in a plate configuration.

By providing a hole between each two seats of each kind, the upper segment near the receiving side of the temperature regulating block is thinned further.

It is advantageous to form the block so that the part underneath the recesses and any holes is a continuous plate. The heat flux is thereby made to pass through a plate segment of very good thermal conductivity which evens the temperatures in the temperature regulating block. The temperature then resulting in the temperature regulating block is essentially determined by the temperature distribution in the plate whereas the part of the temperature regulating block fitted with the recesses laterally taps the plate temperatures without adversely affecting them. A temperature regulating block including a continuous plate segment underneath the part thinned by recesses also is advantageous in implementing a uniform temperature through the entire temperature regulating block when the block is operated without a temperature gradient. The lamellar lower part of the temperature regulating block furthermore assures good contact with temperature-regulating means present therein.

Increased thermal-impedance zones illustratively may be used to control the heat flux in the temperature regulating block, for instance to reduce this flux between adjacent temperature regulators when such are used to generate a temperature gradient. In this manner regulation fluctuations in the temperature regulators may be decreased. These zones also may be used to locally control the temperature gradients, for instance, to control the temperature curve through the full temperature regulating block, illustratively to linearize it. The invention, wherein the zones are grooves, is advantageous over the design of the initially cited art of boreholes. Grooves are more easily made. In particular they begin at the contacting side and thus they thin the continuous plate of the temperature regulating block, contributing predominantly to heat conduction. The grooves in particular may meander between the recesses and holes so as to be a safe distance from said recesses and holes even when the grooves are deep.

Providing several temperature regulators at a contacting side of the block opposite the receiving side allows setting samples at different temperatures in one temperature regulating block. While the initially cited design already allows doing so, it implements this feature by temperature regulators acting on the ends of the temperature regulating block. The invention, on the other hand, offers the advantage that by large-surface contact with the temperature regulating block, the selected temperature profile can be very rapidly achieved over the block's full length and that this block is thermally better controlled against ambient effects. Moreover, the temperature regulating block can be operated at constant temperature in an alternate mode without resort to auxiliary apparatus, whereas the known design requires an additional temperature regulator resting against the contacting side. For that purpose, increased thermal-impedance zones are advantageously provided parallel to the activity boundaries and may directly adjoin them to restrict fluctuations in temperature regulation between the temperature regulators, or they may be mounted above the temperature regulators to control the temperature profile, for instance to linearize it. These zones may be in the form of grooves reducing the block's cross-sectional area. Furthermore, the contacting side may be fitted with temperature regulators split in the longitudinal and transverse directions allowing one to set a temperature profile in either direction, for instance also alternatingly across the temperature regulating block or even in both directions.

It is possible to provide several temperature regulating blocks displaceable relative to a support which supports the receptacles and which can alternatingly move its seats flush with the receptacles. The receptacles in this arrangement, just as in the known design initially discussed, are consecutively engaged by temperature regulating blocks kept at different temperatures and either presenting a temperature gradient or a constant temperature over their surfaces. For the purpose of lateral displacement, the temperature regulating blocks may be mounted in a laterally displaceable carriage. For the same purpose they also may be mounted in a rotor, for instance, rotating like a lazy susan in a plane parallel to the support. Preferably they are rotated by a rotor about an axis parallel to the support to allow especially good compactness. The blocks may be displaced relative to the rotor to achieve spacing or preferably the rotor is displaced as a whole for this spacing motion.

BRIEF DESCRIPTION OF THE DRAWINGS

Embodiments of the invention are illustratively and schematically shown in the accompanying drawings wherein.

DESCRIPTION OF PREFERRED EMBODIMENTS

Figure 1:
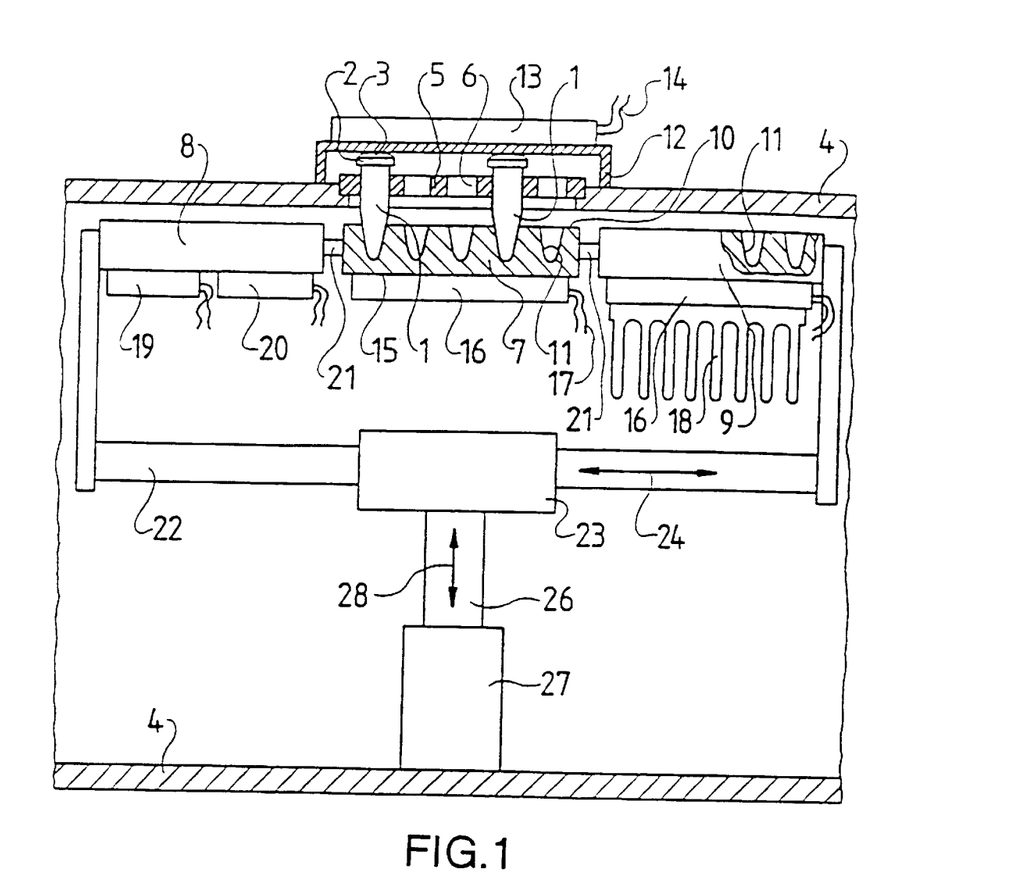
FIG. 1 is a side elevation in section of a thermostatting system for lab work in accordance with the invention fitted with a first embodiment of an alternating block drive.

FIG. 1 shows a lab thermostatting system, especially appropriate for the PCR (poly chain reaction) process. In such a process, sample liquids, for instance reaction mixtures, must be consecutively raised to different temperatures.

Sample liquids are provided in receptacles 1 which, in the shown illustrative embodiments, are commercial reaction vials made of thin-walled plastic. Each vial comprises a cylindrical zone which, as shown in FIG. 1, tapers conically at its lower end region which contains the sample liquid. The upper edge is fitted with a collar 2 and with an elastically deformable cap 3 which seals the receptacle.

The lab thermostatting system shown comprises an enclosing housing 4 with a support 5 at its top side in the form of a plate perforated by holes 6 which keep receptacles 1 in position and secure them at their collars 2 against dropping.

A heat regulating block 7 is mounted underneath support 5 and comprises seats 11 at its receiving side 10 which are in the form of pockets or recesses, the shapes of these seats corresponding to that of the lower ends of receptacles 1. The arrangement of seats 11 in the surface of receiving side 10 of block 7 corresponds to the configuration of holes 6 in support 5, in which seats 11 are aligned with holes 6, all of receptacles 1 in support 5 engaging seats 11 and the lower ends of the receptacles making good thermal surface contact with block 7.

In order to secure good thermal surface contact between receptacles 1 and seats 11 of block 7, a cover plate 12 is mounted above support 5 and presses against elastic caps 3 of receptacles 1. To assure reliable temperature regulation of the sample liquids in receptacles 1 and to prevent condensation on receptacle caps 3, cover plate 12 is raised to a suitable temperature by a temperature regulator 13, for instance a Peltier element with leads 14, that rests against the cover plate.

On its contacting side 15 opposite receiving side 10, block 7 is in contact with a temperature regulator 16. This temperature regulator illustratively may be a Peltier element powered through leads 17. A Peltier element is especially well suited for such purposes because it can serve to heat or cool, depending on need.

Block 7 can be set to the desired temperature by temperature regulator 16. Preferably, a temperature sensor is provided in block 7 for this purpose and at a suitable location which, by means of an electronic regulating device, controls the temperature regulator 16 so that the temperature in block 7 is kept constant at an appropriate level.

If, as shown, block 7 provides surface contact between receptacles 1 and recesses 11, then the sample liquids very quickly and highly accurately assume the temperature of block 7, that is, the desired temperature of reaction.

In the illustrative embodiment shown, the lab thermostatting system comprises two further blocks 8 and 9 with recessed seats 11 corresponding to the already discussed block 7. Temperature regulating blocks 8 and 9 also have temperature regulators, block 9 having a temperature regulator 16 and block 8 having two juxtaposed temperature regulators 19 and 20 which can be operated in parallel to be at the same temperature or alternatively, as described further below, at different temperatures. Temperature regulator 16 underneath temperature regulating block 9 has a cooling body 18 which furthermore may also be present at the other temperature regulators and which is advantageous if the temperature regulator is a Peltier element that must dissipate or accept heat on its surface away from the temperature regulating block.

The configuration of recesses 11 in all three blocks 7, 8 and 9 is identical. Therefore, each of the blocks can be made selectively to engage receptacles 1 in support 5.

A block-exchanging drive is provided for that purpose The blocks 7, 8 and 9 are rigidly interconnected by braces 21 in one plane to a laterally displaceable carriage which rests in a slide guide 23 so as to be longitudinally displaceable in the direction of arrow 24 by a pushrod 22. The lateral drive so constituted for the temperature regulating blocks 7, 8 and 9 is adjustable in height as a whole by a spacing drive.

To implement spacing, slide guide 23 is mounted on a pushrod 26 which is height-adjustably supported for movement in the direction of arrow 28 in a slide guide 27.

Starting with the position of the temperature regulating blocks shown in FIG. 1 wherein the center temperature regulating block 7 engages receptacles 1, block 7 can be disengaged from the receptacles by being lowered by slide guide 27. Thereupon, by adjusting pushrod 22 of the lateral drive, one of the two other blocks can be moved to a flush position underneath support 5 and, following upward displacement inside slide guide 27, can be made to engage receptacles 1.

In this manner receptacles 1 seated in support 5 can be moved alternatingly into thermal contact with temperature regulating blocks 7, 8 or 9. These blocks may be kept regulated at different temperatures. Accordingly, receptacles 1 can be subjected in rapid sequence to different, highly accurate temperatures, a feature which is especially desirable in the PCR procedure.

Just as the holes 6 in the support 5, seats 11 in temperature regulating blocks 7, 8 and 9 may be configured appropriately, for instance in rows and columns. Once cover plate 12 has been removed, the receptacles may be replaced. Illustratively, they may be replaced with support 5 to save time, support 5 then necessarily being replaceable relative to housing 4.

Instead of the shown three temperature regulating blocks 7, 8 and 9, another number may also be used in the shown linear carriage configuration, depending on the number of temperature steps.

Moreover the configuration of lateral drive and spacing drive may be different. Illustratively, the blocks may be connected through individual spacing drives to one lateral drive.

The blocks can be exchanged underneath receptacles 1 manually or preferably using motor drives illustratively controlled by computers and implementing in a way not shown the displacement of pushrod 22 relative to its slide guide 23 and that of pushrod 26 relative to its slide guide 27. In this manner, a temperature-control cycle of desired sequence can be run in accordance with a control program Instead of the block drive shown in FIG. 1 wherein the lateral drive is designed as a slide carriage with slide guide 22, 23, the lateral drive illustratively may also be in the form of a lazy susan. In that case the shown blocks 7, 8 and 9 must be mounted in a plane parallel to the support 5 and pivotable about an axis of rotation perpendicular to said plane.

Figure 2:
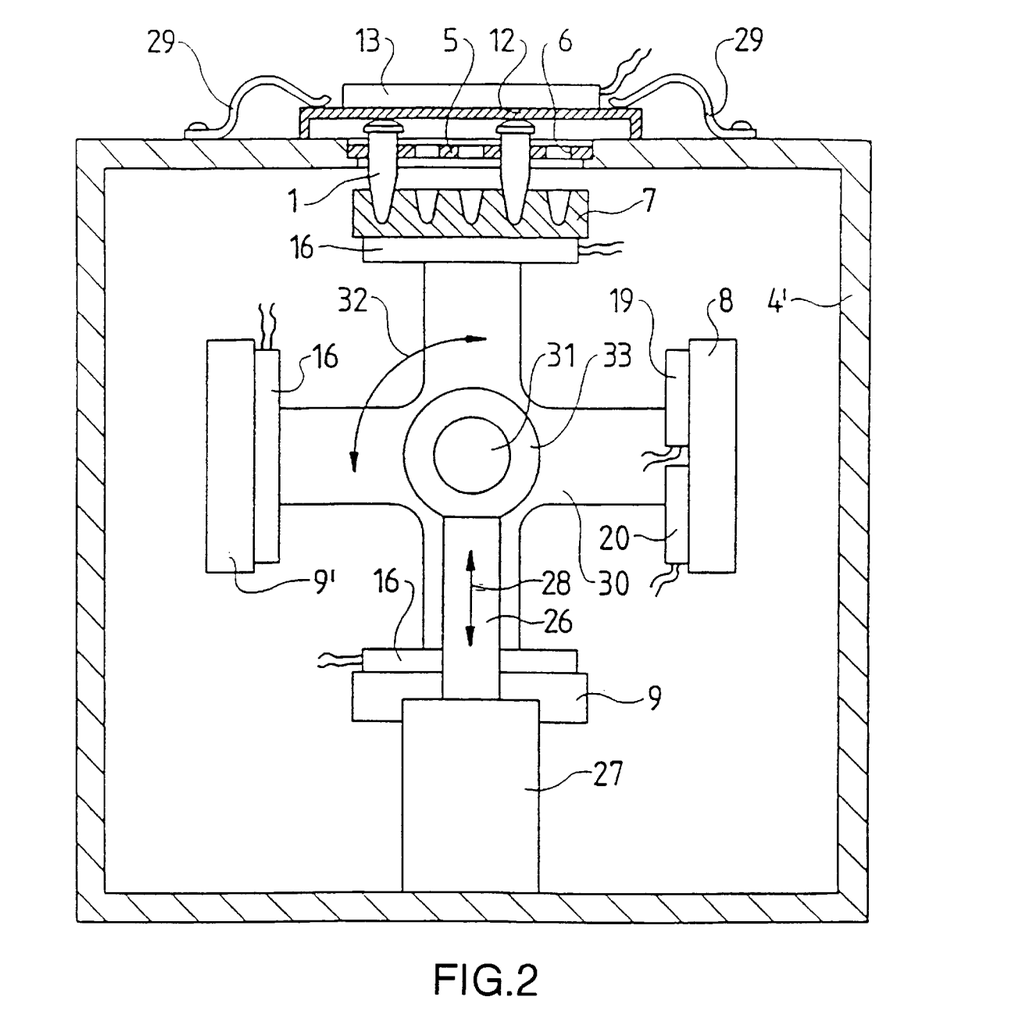
FIG. 2 is a side elevation in section of a lab thermostatting system in accordance with the invention with a second embodiment of an alternating block drive.

FIG. 2 shows a further advantageous embodiment of the block exchanging drive. Parts of the drive structure correspond to that of FIG. 1. As much as possible, the same parts are denoted by the same references.

Support 5 holding receptacles 1 is at the top side of a slightly modified housing 4'. Again it is covered by a cover plate 12 assuring pressure on, and temperature regulation of, the receptacles from above. FIG. 2 additionally shows detachable locking means 29 that also may be provided in the embodiment of FIG. 1 and which secure the cover plate 12 in the shown position.

In the embodiment of FIG. 2, the lab temperature regulating system comprises the three temperature regulating blocks 7, 8 and 9 of FIG. 1 and additionally a temperature regulating block 9' of corresponding design. These temperature regulating blocks, including the associated temperature regulators, correspond to the embodiment of FIG. 1. Temperature regulating block 7 in its shown position engages receptacles 1 flush under support 5.

The lateral motion of the temperature regulating blocks is, however, essentially different in FIG. 2 from that shown in FIG. 1.

Blocks 7, 8, 9 and 9' are affixed at 90° positions to a rotor 30 held in a head 33 of pushrod 26 so as to be rotatable about an axis 31 in the direction of the arrow 32, pushrod 26 being longitudinally displaceable inside slide guide 27 in the direction of arrow 28.

To exchange the temperature regulating blocks underneath support 5, first pushrod 26 together with rotor 30 is moved down until the temperature regulating block previously just engaged is disengaged from receptacles 1. Rotor 30 is then rotated through an angle equal to a multiple of 90° to move another temperature regulating block flush with and underneath support 5 and to bring it into contact with receptacles 1 by raising pushrod 26. In this embodiment, motor drives, not shown, may be provided which illustratively are driven in fully automated manner by a computer control.

Comparison of FIGS. 1 and 2 shows that the embodiment of FIG. 2, employing a rotating drive for the temperature regulating blocks, is more compact.

Figure 3:
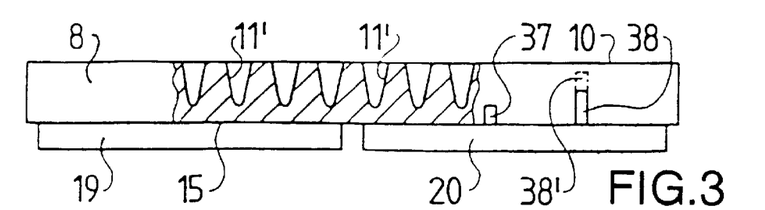
FIG. 3 is a side elevation in partial section of a first embodiment of a temperature regulating block for producing a temperature gradient.

FIG. 3 is a side view of temperature regulating block 8 of FIGS. 1 and 2 and its two temperature regulators 19 and 20 also in side view. Seats 11' used as recesses to hold the receptacles in this embodiment are somewhat smaller in size and larger in number. Seats 11' may be arrayed in rows and columns at the receiving side 10. They serve to receive a substantial number of receptacles which are to be temperature regulated.

Temperature regulators 19 and 20 resting against contacting side 15 of block 8 preferably are Peltier elements fitted with power leads (not shown) from FIG. 3 for power application. As a result, arbitrary temperatures may be implemented in heating or cooling manner. However, temperature regulators 19 and 20 also may be heat exchangers crossed by liquid flows and fed, for instance, by hose systems.

Temperature regulators 19 and 20 may be set at the same or at different temperatures. Temperature sensors in the block, not shown, above the temperature regulators may be connected to a control system controlling the heat input or dissipation implemented by the temperature regulators.

In the embodiment of FIG. 3, temperature regulators 19 and 20 each rest against approximately half of contacting side 15. Good thermal contact can be secured by bonding, screwing or other affixation means.

When temperature regulators 19 and 20 are set at different temperatures, in the case shown with temperature regulator 20 being at the higher temperature, there will ensue a longitudinal temperature function of temperature regulating block 8 shown in FIG. 3. Temperature regulator 20 constantly applies heat to temperature regulating block 8, whereas temperature regulator 9 cools the temperature regulating block, i.e. removes heat from it. Accordingly, a heat flux is set up through temperature regulating block 8 between temperature regulators 20 and 19.

Figure 3A:
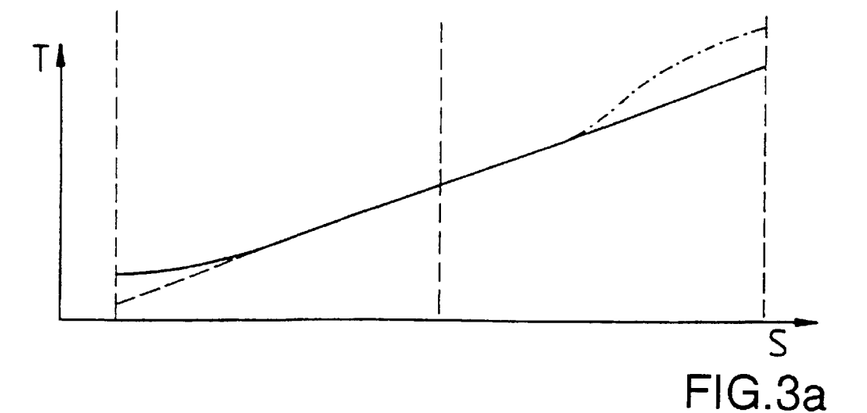
FIG. 3a is a graph of a temperature gradient produced in the block shown in FIG. 3.

The temperature function of FIG. 3a shows the temperature T over the path S in which the temperature function is linear in the middle zone of the temperature regulating block 8. Near the left end, that is above temperature regulator 19, the temperature function becomes shallower because the heating effectiveness of temperature regulator 20 decreases ever more toward the left end of temperature regulating block 8.

At the right side, that is above temperature regulator 20, the temperature is linear to the end of the temperature regulating block as shown by FIG. 3a. This result is assured by two grooves 37 and 38 extending parallel to the boundary between the areas of contacting side 15 contacted by temperature regulators 19 and 20. These grooves reduce the cross-section of the temperature regulating block 8 and assure a local increase in thermal impedance to the heat flux present in the block between the heating and cooling temperature regulators 20 and 19 resp., the block otherwise being of high thermal conductivity and, for instance, made of metal. Because the slope of the temperature gradient of the temperature curve shown in FIG. 3a is proportional to the product of heat flux and thermal impedance, the shape of the temperature curve can be controlled by locally changing the thermal impedance, and in particular, as shown by FIG. 3a, the curve may be made straight. For this purpose, grooves 37 and 38 are of different depths, that is, they reduce the block's cross-section differently. The depth and configuration of grooves 37 and 38 of FIG. 3 is merely illustrative. The exact depth, position and number of grooves illustratively can be determined empirically.

FIG. 3a shows that the temperature slope becomes shallower at the left side of temperature regulating block 8. This flattening is compensated on the right side, that is by means of the temperature regulator 20, by the presence of grooves 37 and 38. As shown by FIG. 3, groove 38 is deeper than the groove 37 because it is nearer the right rim of the block, that is, in a zone wherein the heat flux from temperature regulator 20 to temperature regulator 19 is less than at the site of groove 37. To implement the same temperature gradient at groove 38, higher thermal impedance, namely a deeper groove, is required. If groove 38 is deepened further, as indicated by broken lines 38', the temperature profile can be raised further in this zone as indicated by dash-dot lines in FIG. 3a.

Figure 4:
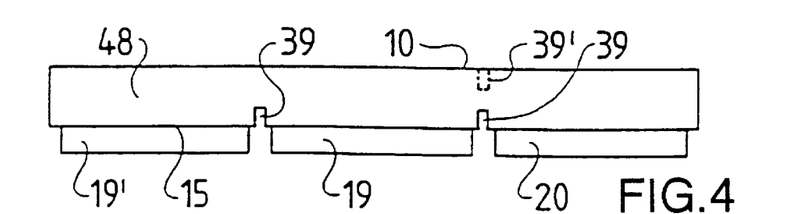
FIG. 4 is a side elevation of a second embodiment of a temperature regulating block to produce a temperature gradient.
Figure 4A:
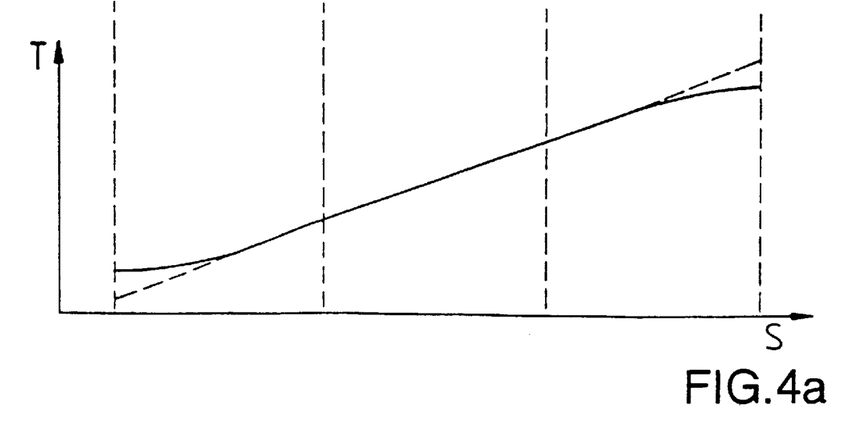
FIG. 4a is a graph of a temperature gradient in the block of FIG. 4.

FIG. 4 is a view similar to FIG. 3 of a temperature regulating block 48 comprising three temperature regulators 19', 19 and 20. If temperature regulator 20 is heating and temperature regulator 19 is cooling, the temperature is as shown by the curve in FIG. 4a. At the ends of the curve, that is above temperature regulators 19' and 20, the slope is shallower for lack of grooves above the temperature regulators such as the grooves 37 and 38 of FIG. 3.

A linear temperature gradient is implemented by means of middle temperature regulator 19. Middle temperature regulator 19 can be operated at an intermediate temperature or, where called for, it may be shut off. It is needed to prevent any temperature-curve deviation at the middle of the block and in particular also when the temperature curve as a whole must be rapidly shifted to another level. It is also needed in the alternative of the total block being set to the same temperature.

The temperatures must be regulated to achieve the required exact temperature in temperature regulating block 48. For that purpose, temperature regulators 19', 19 and 20 are each controlled in its own control loop by sensors (not shown) mounted in block 48 above the individual temperature regulators. Heat exchange takes place between the control loops by heat flux in the block between the temperature regulators. As a result, the control loops interact and control fluctuations may arise which can be checked only with difficulty.

The fluctuations in regulation can be reduced by reducing the heat flux between the temperature regulators. In the embodiment of FIG. 4, grooves 39 increasing the thermal impedance between the temperature regulators are provided for such a purpose at the boundaries between the areas of contacting side 15 that are fitted with the temperature regulators 19', 19 and 20.

As further shown by FIG. 4, grooves 39 also may be machined from above, that is into the receiving side, as indicated in dashed lines by the groove 39'. The grooves 37 and 38 of FIG. 3 alternatively also may be fitted into the block from above, that is into the receiving side 10.

Grooves 37, 38 and 39 are shown in FIGS. 3 and 4 that are designed to hamper the heat flux in the temperature regulating block for a variety of purposes, by reducing block cross-section, i.e. increasing its thermal impedance. However, other zone-designs also may be used instead of the shown grooves in the temperature regulating block, offering a different thermal conductivity or thermal impedance from the other segments of the block. The grooves may be replaced, for instance, by zones in the temperature regulating block comprising a thermal conductivity, or impedance, different from other block regions. Illustratively, such zones may be created by splitting the block at this location and by sandwiching an insert of a material of higher thermal impedance into the block. These zones, just as the grooves shown in FIGS. 3 and 4, can pass through in arbitrary linear manner, preferably, however, transversely to the heat flux and in a straight line between two edges of the block. Illustratively, the grooves shown in FIGS. 3 and 4 preferably run transversely to block 8 or 48, that is perpendicular to the plane of the paper and through the entire block.

Each temperature regulating block 8 and 48 shown in FIGS. 3 and 4 is fitted with two temperature regulators 19, 20 or three temperature regulators 19, 19' and 20, which in each case cover the full width of the block. As shown by the temperature functions of FIGS. 3a and 4a, a temperature gradient in this block therefore can be set up only in the longitudinal direction, that is from left to right in the drawing.

Figure 5:
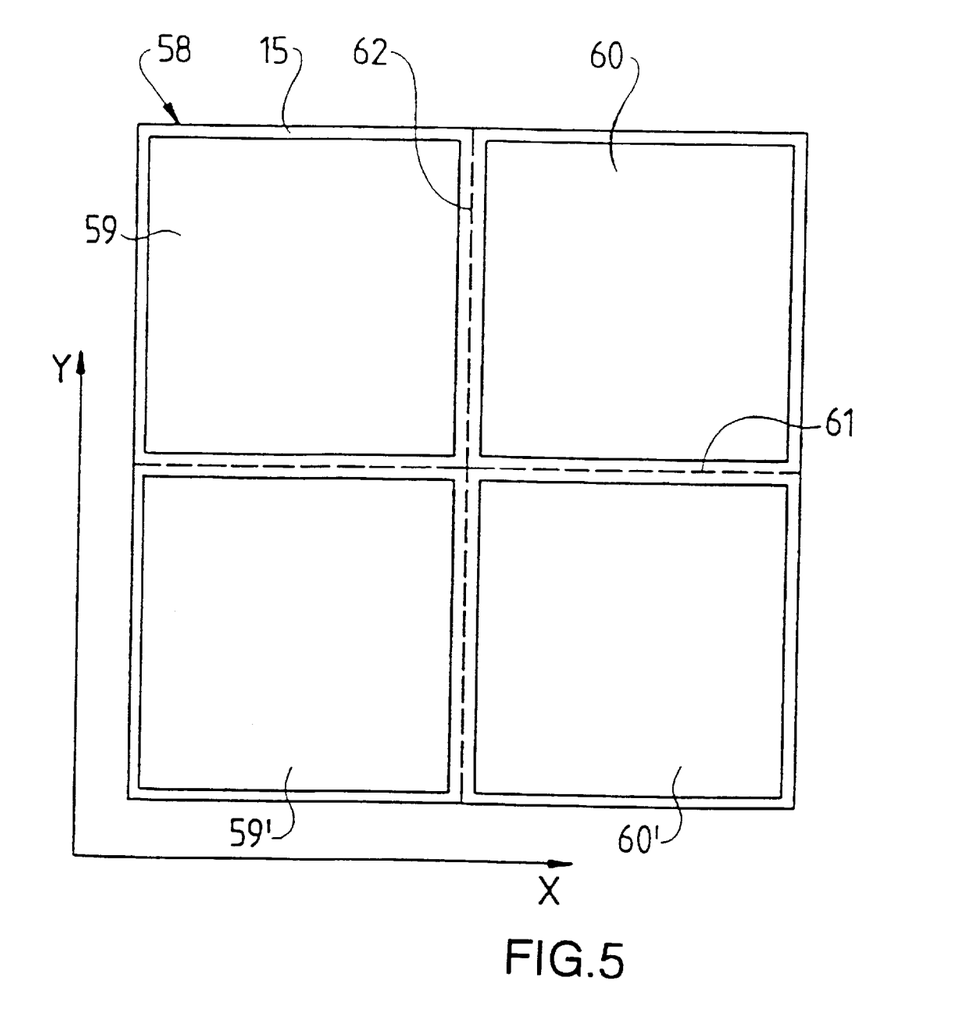
FIG. 5 is a plan view of a temperature regulating block at the contacting side with four quadrant-mounted temperature regulators.

FIG. 5 shows a variation of a temperature regulating block 58 in which the contacting side 15 is fitted with segment boundaries 61 and 62 and with temperature regulators 59, 60, 59' and 60' in four quadrants. If temperature regulators 59 and 59' are operated in an identical manner, for instance in the cooling mode, and if the temperature regulators 60 and 60' are operated at the same temperature, a temperature gradient in the direction of the x-axis is set up in temperature regulating block 58. If temperature regulators 59 and 60 and also temperature regulators 59' and 60' are operated at the same temperature, then a temperature gradient is set up in the perpendicular direction, i.e. in the y-axis direction. If all temperature regulators are operated at the same temperature, a constant temperature will be implemented over the entire temperature regulating block 58.

The ability to generate a temperature gradient alternatingly in the x- or y-direction makes possible an operational variation wherein the temperature regulating block 58 is operated successively at two different temperature levels, for instance one at 30° C. and one at 60° C. At each level, the precisely optimal temperature is determined: this goal may be implemented in one pass, first the temperature regulating block being operated at the 30° C. level in the x-direction at a gradient, this gradient for instance generating temperatures at the temperature regulating block of 28, 29, 30, 31, 32° C. Thereupon the temperature regulating block is set at the 60°

C. temperature with a temperature gradient in the y-direction, different temperatures for instance of 58, 59, 60, 61, 62° C. being produced in the y-direction. If in the process the temperature regulating block holds samples to be temperature-regulated and arrayed over its surface in regular rows (x direction) and columns (y direction), then such samples can next be analyzed and those that were optimally temperature regulated can be determined. As regards the latter, they had been subjected to the optimal temperature at each temperature level.

A further operational variation is significant, namely one wherein all four temperature regulators are kept at different temperatures. In such a case a complex temperature function can be applied with temperatures differing both in the x and in the y directions. Illustratively, a larger temperature gradient can be set, for instance, in the x direction and a smaller one in the y direction. If seats are provided at the receiving side of temperature regulating block 58 to accept receptacles in rows (x direction) and columns (y direction), then illustratively temperature differences of 1° C. may be set between the rows and temperature differences of 0.1° C. between the columns. As a result, temperature differentials of 10° C. with a resolution of 0.1° C. can thus be set.

Figure 6:
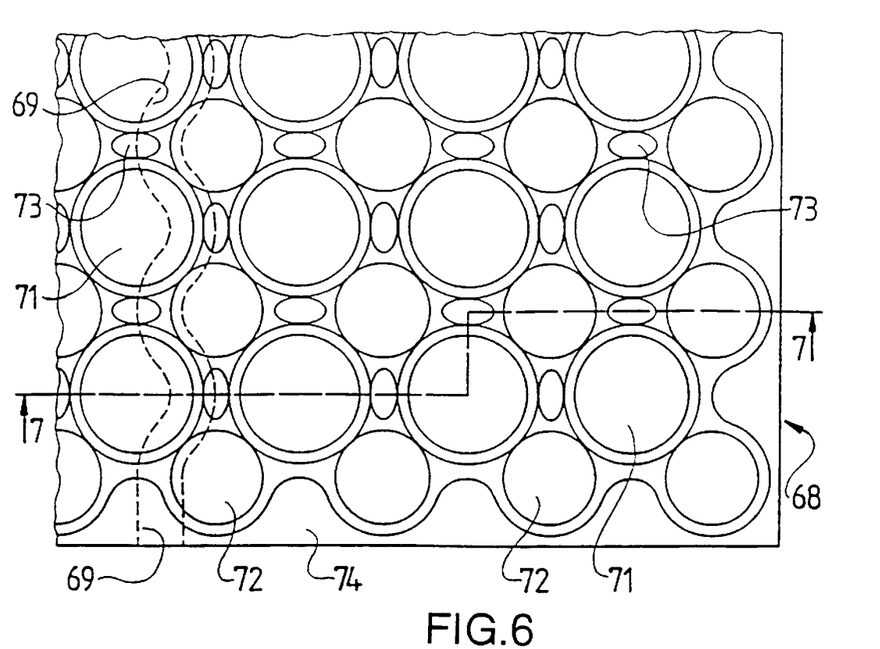
FIG. 6 is a top plan view of a temperature regulating block corresponding to that of FIG. 4 and with a detailed view of the seats.
Figure 7:
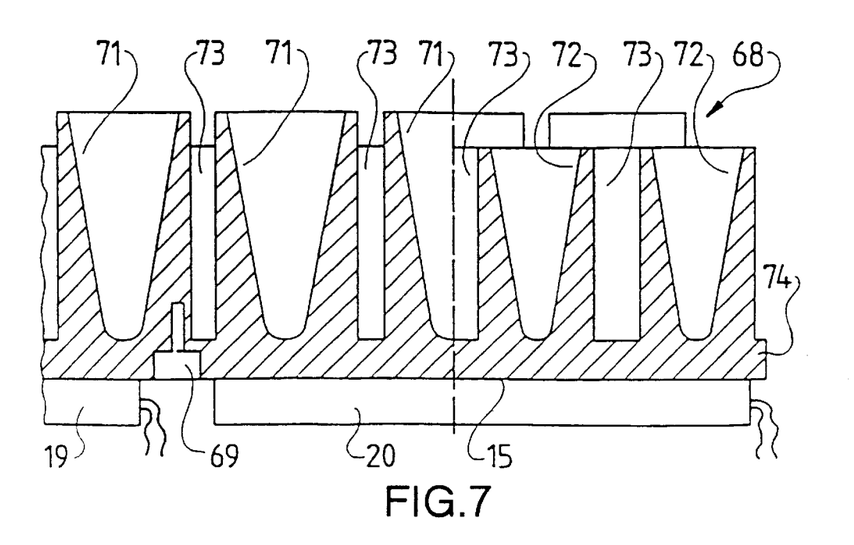
FIG. 7 is a section along line 7—7 of FIG. 6.

FIGS. 6 and 7 are resp. a top view of the receiving side and a cross-section of a temperature regulating block 68 of which the configuration substantially corresponds to that of the already discussed temperature regulating block 8, that is, being in contact at its contact side 15 with two temperature regulators 19 and 20.

Two different kinds of seats 71 and 72 in the form of recesses of different depths are formed in the receiving side.

As shown in FIG. 6, the two kinds of seats 71 and 72 nest among each other in a rectangular grid pattern in such a way that a seat 72 of the second kind is each time located between four seats 71 of the first kind, and vice-versa. As shown in FIG. 7, the block thereby assume a filigree construction of much reduced cross-section in the upper portion of the block, that is toward its receiving side. In addition, oval holes 73 are inserted between seats 71 and 72, each being located centrally between two larger seats 71 and two smaller seats 72, as shown in FIG. 6. Temperature regulating block 70 as a result is additionally thinned in its upper portion. Therefore, the heat conduction between the temperature regulators 20 and 19 is less in its upper portion thinned by the seats 71, 72 and the holes 73 than in the zone of the lower, continuous plate 74 running continuously underneath all seats 71, 72 and holes 73.

As shown in FIG. 6, in this embodiment, the volume of temperature regulating block 68 is substantially reduced, in particular at its thick upper zone away from the contacting side 15. As a result, the heat capacity of the temperature regulating block is much reduced. It follows that the temperature regulating block can be made to assume very rapidly a desired temperature, for instance cooling it or heating it to another temperature level. Accordingly, in the lab thermostatting system shown in FIG. 1 or 2, one of the shown temperature regulating blocks can be operated consecutively at different temperature levels. In particular, neighboring temperature levels may be implemented in one temperature regulating block whereas another temperature regulating block is used for a more remote temperature level. As regards the conventional three temperature levels for PCR, illustratively two temperature levels may be implemented in one block and another in a second block. The large area of contact between the temperature regulating block and the temperature regulators shown in the Figures helps much to achieve quick heating or cooling.

The design for low mass of the temperature regulating block 68 shown in FIGS. 6 and 7 assures not only much reduced heat capacity of the temperature regulating block but also offers reduced thermal conductivity, i.e. high thermal impedance of the temperature regulating block in the direction of heat flux between the temperature regulators 20 and 19. To implement a desired temperature profile, i.e. temperature gradient as illustratively shown in FIGS. 3a and 4a, only a low heat flux is needed because of the high thermal impedance. Therefore the temperature regulators 19 and 20 need only offer low power.

Temperature regulating block 68 shown in FIGS. 6 and 7 comprises a groove 69 used to thermally decouple the temperature regulators 20 and 19 from each other as explained in relation to FIG. 4. As sectionally shown in FIG. 7, groove 69 is stepped in order to penetrate as deeply as possible between the seats 71, 72 and holes 73 without, however, touching them. As shown in dashed lines in FIG. 6, groove 69 accordingly meanders between the recesses and holes. Illustratively, the shown temperature regulating block 68, for instance of aluminum, may be mold-cast or be manufactured with a numerically controlled milling machine.

In a manner to groove 39 shown in dashed lines in FIG. 4, groove 69 of FIGS. 6 and 7 can be machined on the receiving side, that is from above into the temperature regulating block 68. Illustratively, this groove 69 may run transversely through recesses 71, 72 and holes 73, or it may meander around them, for instance in the form of a very narrow and deep slit.

What is claimed is:

1. A temperature regulating block for a laboratory thermostating system, comprising:

a body having a receiving side;

a plurality of first recesses for receiving first receptacles and dimensioned to provide a large-area contact between each of the first recesses and a respective first receptacle, whereby a heat transfer relationship between the body and the first receptacles is provided;

a plurality of second recesses for receiving second receptacles and dimensioned to provide a large-area contact between each of the second recesses and a respective second receptacle, whereby a heat transfer relationship between the body and the second receptacles is provided; and at least one temperature regulator in contact with the body, wherein the first recesses and the second recesses are arranged in a regular, two-dimensional grid such that each of the first recesses is located between four second recesses, and each of the second recesses is located between four first recesses, wherein the receiving side has a plurality of holes, with each hole being located between two first recesses and two second recesses, and wherein the at least one temperature regulator comprises a continuous plate arranged underneath the first and second recesses and the holes.

2. A temperature regulating block according to claim 1, wherein the body comprises a groove forming a zone of thermal impedance higher than thermal impedance of a remainder of the body.

3. A temperature regulating block according to claim 2, wherein the body has a contacting side opposite the receiving side, and the groove is formed in the contacting side.

4. A temperature regulating block according to claim 3, wherein the groove has a depth larger than a thickness of the continuous plate and meanders between the first and second recesses and the holes.

5. A temperature regulating block for a laboratory thermostating system, comprising:

a body having a receiving side;

a plurality of first recesses for receiving first receptacles and dimensioned to provide a large-area contact between each of the first recesses and a respective first receptacle, whereby a heat transfer relationship between the body and the first receptacles is provided;

a plurality of second recesses for receiving second receptacles and dimensioned to provide a large-area contact between each of the second recesses and a respective second receptacle, whereby a heat transfer relationship between the body and the second receptacles is provided; and at least one temperature regulator in contact with the body, wherein the first recesses and the second recesses are arranged in a regular, two-dimensional grid such that each of the first recesses is located between four second recesses, and each of the second recesses is located between four first recesses, wherein the body has a contacting side opposite the receiving side, and wherein the temperature regulating block comprises a plurality of temperature regulators arranged at the contacting side and forming a large-area contact with respective segments of the contacting side, the plurality of temperature regulators regulating the respective segments at different temperatures.

6. A temperature regulating block for a laboratory thermostating system, comprising:

a body having a receiving side;

a plurality of first recesses formed in the receiving side for receiving first receptacles and having a first diameter;

a plurality of second recesses formed in the receiving side for receiving second diameter different from the first diameter; and at least one temperature regulator in contact with the body, wherein the plurality of first recesses and the plurality of second recesses are arranged in respective plane rectangular grids arranged parallel to each other and offset relative to each in opposite directions of the grid by ½ grid constant; and wherein the grid constant and the first and second diameters are so selected that each of the first recesses and each of the second recesses are separated, respectively, from four second recesses and four first recesses by narrow webs.

* * * * *